(12) United States Patent
Jia et al.

(10) Patent No.: US 6,403,676 B1
(45) Date of Patent: *Jun. 11, 2002

(54) DENTAL COMPOSITES COMPRISING GROUND, DENSIFIED, EMBRITTLED GLASS FIBER FILLER

(75) Inventors: Weitao Jia, Wallingford; Martin L. Schulman, Orange; Arun Prasad, Cheshire; Bruce Alpert, Madison, all of CT (US)

(73) Assignee: Jeneric/Pentron Incorporated, Wallingford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/461,576

(22) Filed: Dec. 15, 1999

Related U.S. Application Data (63) Continuation of application No. 09/092,370, filed on Jun. 5, 1998, now abandoned, which is a continuation of application No. 08/951,414, filed on Oct. 16, 1997, now Pat. No. 6,013,694.

(51) Int. Cl.$^7$ ............................. A61K 6/083; C08K 3/40
(52) U.S. Cl. .................... 523/116; 65/33.1; 65/33.7; 65/442; 433/215; 501/69; 523/116; 524/450; 524/494
(58) Field of Search ............................. 523/115, 116; 524/494, 450; 501/69; 65/33.1, 33.7, 442; 433/215

(56) References Cited

U.S. PATENT DOCUMENTS

| | | | |
|---|---|---|---|
| 2,477,268 A | 7/1949 | Saffir | 523/115 |
| 2,514,076 A | 7/1950 | Kelly | 523/109 |
| 3,066,112 A | 11/1962 | Bowen | 523/116 |
| 3,096,144 A | 7/1963 | Wainer et al. | 501/85 |
| 3,179,623 A | 4/1965 | Bowen | 528/205 |
| 3,194,784 A | 7/1965 | Bowen | 523/116 |
| 3,328,230 A | 6/1967 | Levecque et al. | 65/376 |
| 3,751,399 A | 8/1973 | Lee et al. | 106/35 |
| 3,923,740 A | 12/1975 | Schmitt et al. | 523/116 |
| 3,926,906 A | 12/1975 | Lee, II et al. | 523/116 |
| 4,017,454 A | 4/1977 | Muller | 523/117 |
| 4,174,334 A | 11/1979 | Bertenshaw et al. | 106/35 |
| 4,209,434 A | 6/1980 | Wilson et al. | 523/116 |
| 4,215,033 A | 7/1980 | Bowen | 523/115 |
| 4,381,918 A | 5/1983 | Ehrnford | 433/199 |
| 4,392,828 A | 7/1983 | Ehrnford | 433/217 |
| 4,427,799 A | 1/1984 | Orlowski et al. | 523/116 |
| 4,500,657 A | 2/1985 | Kumar | 527/117 |
| 4,514,174 A | 4/1985 | Dougherty et al. | 433/226 |
| 4,544,359 A | 10/1985 | Waknine | 523/115 |
| 4,547,531 A | 10/1985 | Waknine | 523/116 |
| 4,674,980 A | 6/1987 | Ibsen et al. | 523/116 |
| 4,707,504 A | 11/1987 | Walkowiak et al. | 523/113 |
| 4,717,341 A | 1/1988 | Goldberg et al. | 433/9 |
| 4,731,394 A | 3/1988 | Vogel et al. | 523/115 |
| 4,744,759 A | 5/1988 | Bowen | 433/226 |
| 4,793,809 A | 12/1988 | Sigler et al. | 433/218 |
| 4,894,012 A | 1/1990 | Goldberg et al. | 523/115 |
| 4,952,530 A | 8/1990 | Brosnan et al. | 501/39 |
| 4,997,373 A | 3/1991 | Tanaka et al. | 433/204 |
| 5,078,596 A | 1/1992 | Carberry et al. | 433/8 |
| 5,081,164 A | 1/1992 | Lai | 523/116 |
| 5,084,491 A | 1/1992 | Kerby | 523/116 |
| 5,266,609 A | 11/1993 | Hall et al. | 523/116 |
| 5,276,068 A | 1/1994 | Waknine | 523/116 |
| 5,378,737 A | 1/1995 | Jacobs et al. | 523/116 |
| 5,549,123 A | 8/1996 | Okuyama et al. | 433/201.1 |
| 5,621,035 A | 4/1997 | Lyles et al. | 524/404 |
| 5,676,745 A | 10/1997 | Kelly et al. | 106/35 |
| 5,788,499 A | 8/1998 | Hoffman | 433/226 |
| 5,969,000 A | 10/1999 | Yang et al. | 523/116 |
| 6,013,694 A | * 1/2000 | Jia et al. | 523/116 |
| 6,030,220 A | * 2/2000 | Karmaker et al. | 433/215 |

FOREIGN PATENT DOCUMENTS

| | | |
|---|---|---|
| DE | 43 23 143 C | 12/1994 |
| FR | 2 416 074 | 8/1979 |

OTHER PUBLICATIONS

Jiri Militky and Vladimir Kovacic, "Ultimate Mechanical Properties of Basalt Filaments" Textiles Res. J, vol. 66, No. 4, pp. 225–229 (1996).

DENTSPLYCaulk, SURE FILL, High Density Posterior Restorative, Technical Manual, pp. 1–23.

K. F. Leinfelder et al, A New Polymer Rigid Matrix Material, CDA Journal, Sep. 1996, pp. 78–82.

* cited by examiner

Primary Examiner—Peter Szekely
(74) Attorney, Agent, or Firm—Cantor Colburn LLP (57) ABSTRACT

A composite for a dental restoration is presented comprising ground, densified, embrittled glass fibers together with fillers and a polymeric matrix precursor composition. The ground, densified, embrittled glass fibers are obtained by grinding glass fibers which have been densified and embrittled by heating glass fibers at a temperature substantially below the softening point of the glass fibers, without significant fusion or melting together of the fibers. The composite is particularly useful as a direct filling material, in that it has the feel and workability of an amalgam.

15 Claims, 3 Drawing Sheets

DENTAL COMPOSITES COMPRISING GROUND, DENSIFIED, EMBRITTLED GLASS FIBER FILLER

CROSS-REFERENCE TO RELATED APPLICATIONS

This is a continuation of application Ser. No. 09/092,370 filed Jun. 5, 1998 entitled DENTAL COMPOSITES COMPRISING GROUND, DENSIFIED, EMBRITTLED GLASS FIBER FILLER, now abandoned, which is a continuation of application Ser. No. 08/951,414 filed Oct. 16, 1997 entitled DENTAL COMPOSITES COMPRISING GROUND, DENSIFIED, EMBRITTLED GLASS FIBER FILLER, now U.S. Pat. No. 6,013,694.

BACKGROUND OF THE INVENTION

1. Field of the Invention

This invention relates to dental composite materials and methods of manufacture thereof. In particular, this invention relates to improved glass fiber fillers for dental composite materials, wherein the glass fibers are densified and embrittled by heating the fibers.

2. Brief Discussion of the Related Art

Compositions useful for repairing damaged teeth in situ are known in the art as direct filling materials, and include alloys and resin composites. Dental amalgam alloys have widely been used as direct filling material, and provide excellent handling characteristics, and physical properties. The technique of mechanically packing and condensing a material into a tooth cavity is previously known to the dental profession with the use of dental amalgams in connection as a direct filling material. It has well known advantages in that it permits a close adaptation of the filling material to the cavity walls and also makes it possible to make firm contacts between the restored tooth and its neighbor. Further, it makes it possible to give the restoration its final anatomic form before hardening, thereby avoiding the time consuming and difficult finishing work with rotating instruments required with composite materials. These advantages are achieved by the densified, embrittled glass fiber composites on the present invention and the method of manufacture thereof. However, there are perceived health hazard concerns regarding the use of high amounts of mercury or gallium present in amalgam alloys.

Dental resins have accordingly been developed, which comprise polymeric matrices, for example polyamides, polyesters, acrylates, polyolefins, polyimides, polyarylates, polyurethanes, vinyl esters, or epoxy-based materials. Other polymeric matrices include styrenes, styrene acrylonitriles, acrylonitrile butadiene styrene polymers ("ABS polymers"), polysulfones, polyacetals, polycarbonates, polyphenylene sulfides, and the like. The most popular polymeric matrices are based on monomers having at least one ethylenically unsaturated group, in particular acrylate and methacrylate groups. One commonly used monomer of this class is the reaction product of bisphenol A with glycidyl methacrylate (hereinafter BIS-GMA). In addition, these resins have also been used to make artificial teeth and denture basis.

Unfilled (i.e., pure) curable acrylic and methacrylic resins generally suffer from polymerization shrinkage and poor durability. These drawbacks have been reduced in direct filling applications, in part, through the addition of inert fillers. See, for example, U.S. Pat. No. 3,066,112 which is herein incorporated by reference. The combination of binder plus filler is commonly referred to as a composite direct filling material. Currently used fillers for curable dental resins generally are inert materials in the form of finely divided irregular particles, fibers or beads, present in an amount from about 35 to about 80 percent by weight of the total composite direct filling material.

Commonly used inorganic fillers include fumed silica, quartz, glass, various mineral silicates (e.g., β-eucryptite, lepidolite, petalite, spondumene, beryl, topaz and zircon), silicon carbide, alumina, and mixtures thereof. Commonly-assigned U.S. Pat. No. 4,544,359 to Waknine, for example, discloses a filler mixture comprising barium silicate, borosilicate glass, and colloidal silica. In general composite direct filling materials which are fully loaded with inorganic fillers (i.e. combined with the highest workable volume loading) having particles in the range of 0.01–1.2 microns are the most wear-resistant currently available composite direct filling materials. However, these composite direct filing materials containing finely divided inorganic fillers and acrylic binder resins may not polish as easily as unfilled dental resin.

Organic materials have also been used as fillers. For example, U.S. Pat. No. 3,923,740 discloses a direct filling material containing finely divided cured polymethyl methacrylate, alone or in conjunction with an inorganic filler. Composite direct filling materials which are wholly or partly filled with finely divided polymethyl methacrylate have better polishability (i.e. better surface finish after polishing with ordinary dental tools) than composite direct filling materials which are fully loaded with inorganic fillers, but generally have poorer durability (i.e. poorer wear resistance in vivo) than composite direct filling materials having inorganic fillers only.

Regarding fibrous fillers in particular, U.S. Pat. No. 2,477,268 to Saffir discloses short glass fibers randomly dispersed in dental resin materials, as does U.S. Pat. No. 2,514,076 to Kelly. Use of long, fully wetted fibers in structural components for dental restorations and the like are disclosed in U.S. Pat. No. 4,894,012 to Goldberg et al. However, none of these patents is discloses a composite having the feel of amalgam.

Fused-fibrous filler compositions in the dental arts are also known. Such fused fibrous fillers are of particular interest because they reportedly provide a feel similar to that of amalgam when used by the dentist, and may be applied using similar techniques. In U.S. Pat. No. 4,381,918 and U.S. Pat. No. 4,392,828 to Ehrnford there is disclosed a filler comprising porous inorganic particles which are completely or partially impregnated with a resin material. The porous inorganic particles are formed by heating inorganic fibers under pressure to fuse the fibers at their points of contact, thereby forming a rigid three-dimensional network of inorganic fibers. Fused-fibrous fillers compositions are also disclosed in U.S. Pat. No. 5,621,035 to Lyles et al. Such fillers comprise silica fibers together with either alumina or aluminosilicate fibers which are fused in the presence of a fusion source such as boron nitride. The presence of boron lowers the melting point of the fibers sufficiently to allow formation of a porous, interconnected network. The network is then ground to particles having a size of about 180 microns, and used as fillers in dental composites.

Unfortunately, use of the fused-fibrous filler compositions disclosed in the Ehrnford and Lyles patents requires multiple steps and extensive preparation time. Accordingly, there is a need in the dental arts to develop a dental resin composite which is similar to or approaching to dental amalgam alloys in handling characteristics, physical properties, and applications without the drawbacks and deficiencies associated with dental amalgam alloys, and without the multiple preparation steps required for fused-fibrous compositions.

SUMMARY OF THE INVENTION

The above-described and other problems and deficiencies of the prior art are overcome or alleviated by the composition and method of manufacture of the present invention, comprising ground, densified, embrittled glass fiber fillers and a polymeric matrix. In accordance with the present invention, glass fibers are densified and embrittled by heating the glass fibers at an effective temperature substantially below the softening point of the glass fibers such that the glass fibers are densified and embrittled, which as used herein excludes fusing or melting together. The densified, embrittled fibers are then ground to a fibrous particle size preferably less than about 80 microns ($\mu$m). The ground, densified, embrittled glass fibers of the present invention are preferably used as a filler component of a dental composite, being present in the range from about 5% to about 95% by weight of the total composition, depending upon the use made of the polymerized composition. In addition to the ground, densified, embrittled glass fibers, the polymeric matrix may further comprise other fillers known in the art.

The resulting dental composite exhibits handling characteristics similar to or approaching that of dental amalgam, and is particularly a suitable substitute filling for amalgam without the alleged health hazard concerns. The physical properties of the dental composite of the present invention include a modulus of elasticity of greater than approximately 15 GPa and modulus range between approximately 15 and approximately 22 GPa which is much higher than conventional dental composites which possess an elastic modulus of approximately 10 GPa. The elastic modulus of the composite of the present invention is comparable to amalgam which exhibits an elastic modulus of approximately 20 GPa. A relatively low modulus may cause a temporary displacement of the restoration resulting from normal masticatory stresses. Eventually this may cause leakage that may lead to secondary caries. Such movement or displacement is less likely to occur with materials having a high elastic modulus such as the composite of the present invention. Further, the composite exhibits a Vicker's hardness of greater than 1000 MPa and preferably approximately 1,250 MPa enabling it to withstand stress better than conventional dental composites having a hardness in the range of 600 to 700 MPa. The wear rate is very low, averaging about 3.5 microns per year which is comparable to that exhibited by amalgam. The water sorption of the composite of the present invention is no greater than approximately 10 micrograms per cubic millimeter per week ("$\mu$g/mm$^3$/wk") and preferably approximately 8.9 $\mu$g/mm$^3$/wk and polymerization shrinkage by volume is approximately 1.98%. The depth of cure of the composite is at least 5 mm which allows for bulk-fill application which is partly a result of the glass fibers used in the filler component. The fibers possibly serve as transparent pipes which transmit light to the bottom of the restoration.

The above-discussed and other features and advantages of the present invention will be appreciated and understood by those skilled in the art from the following detailed description and drawings.

BRIEF DESCRIPTION OF THE DRAWINGS

For the purpose of illustrating the invention, there are shown in the drawing forms which are presently preferred; it being understood, however, that this invention is not limited to the precise arrangements and instrumentalities shown. Referring now to the drawings wherein like elements are numbered alike in the several Figures.

DETAILED DESCRIPTION OF THE INVENTION

The present invention is a dental restoration material comprising a polymeric matrix and ground, densified, embrittled glass fibers, wherein the glass fibers have been densified and embrittled by heating the glass fibers at a temperature substantially below the softening point of the glass fibers. Glass fibers as ordinarily provided by the manufacturer tend to be less dense, and somewhat flexible, that is, capable of being bent without breaking. As used herein, the term "densify" means to cause the fibers to become more dense, that is, to shrink in volume with practically no fusing or melting together of the fibers at their points of contact. "Embrittled" as used herein means to cause the fibers to become more prone to breakage upon the application of force, with practically no fusing or melting together of the fibers at their points of contact. Further as used herein, the term "substantially below" refers to a temperature effective to densify and embrittle the glass fibers, but not to fuse or melt the glass fibers together at their points of contact. The densified, embrittled glass particles are then cooled and ground to a particle size less than about 80 microns according to grinding methods known in the art.

A number of glass compositions are suitable for use in the practice of the present invention, including but being limited to known glasses listed in the Table below. A preferred glass composition is fibers comprising S-2 GLASS®, which is commercially available from Owens Corning. Such fibers have diameters of about 10 microns.

| Oxide* | A-Glass | C-Glass | D-Glass | E-Glass | ECR-Glass® | AR-Glass | R-Glass | S-2 Glass® |
|---|---|---|---|---|---|---|---|---|
| SiO$_2$ | 63–72 | 64–68 | 72–75 | 52–56 | 54–62 | 55–75 | 55–65 | 64–66 |
| Al$_2$O$_3$ | 0–6 | 3–5 | 0–1 | 12–16 | 9–15 | 0–5 | 15–30 | 24–25 |
| B$_2$O$_3$ | 0–6 | 4–6 | 21–24 | 5–10 |  | 0–8 |  |  |
| CaO | 6–10 | 11–15 | 0–1 | 16–25 | 17–25 | 1–10 | 9–25 | 0–0.1 |

-continued

| Oxide* | A-Glass | C-Glass | D-Glass | E-Glass | ECR-Glass ® | AR-Glass | R-Glass | S-2 Glass ® |
|---|---|---|---|---|---|---|---|---|
| MgO | 0–4 | 2–4 | | 0–5 | 0–4 | | 3–8 | 9.5–10 |
| ZnO | | | | | 2–5 | | | |
| BaO | | 0–1 | | | | | | |
| Li$_2$O | | | | | | 0–1.5 | | |
| Na$_2$O + K$_2$O | 14–16 | 7–10 | 0–4 | 0–2 | 0–2 | 11–12 | 0–1 | 0–0.2 |
| TiO$_2$ | 0–0.6 | | | 0–1.5 | 0–4 | 0–12 | | |
| ZrO$_2$ | | | | | | 1–18 | | |
| Fe$_2$O$_3$ | 0–0.5 | 0–0.8 | 0–0.3 | 0–0.8 | 0–0.8 | 0–5 | | 0–0.1 |
| F$_2$ | 0–0.4 | | | 0–1 | | 0–5 | 0–0.3 | |
| Softening point, ° C. | 705 | 750 | 771 | 846 | 882 | 773 | 952 | 1056 |

*Percent by weight

In the practice of the present invention, glass fibers are densified and embrittled by heating at a temperature substantially below the softening point of the glass for a time effective to densify the glass. Such temperature and time are interdependent, and are empirically determined, based on the composition (and thus the softening point) of the glass. Higher temperatures will generally result in shorter times. The temperature must be high enough to effect densification and embrittlement, but not so high as to cause fusion, while the time of heating must be such as to allow even heating, but again, no fusion of the fibers at the chosen temperature.

In a preferred embodiment, at atmospheric pressure, the temperature is at least about 75° C. below the softening point of the glass, and more preferably, at atmospheric pressure, the temperature is between about 100° C. and about 140° C. below the softening point of the glass. S-2 GLASS®, for example, has a softening point of 1056° C. In accordance with the present invention, the S-2 GLASS® fibers are preferably heated at a temperature between about 920° C. to about 950° C. for about 0.5 to 4 hours, a time period effective to densify the glass fibers but not fuse or melt the glass fibers together. In a particularly preferred embodiment, the S-2 GLASS® fibers are heated at a temperature of about 940° C. for about 2 hours.

After densification, the glass fibers are ground to a size suitable for use as a filler in a dental restoration, preferably below about 100 microns. As used herein, grinding refers to any known methods for size reduction, including reduction to spherical or fiber form. To obtain the desired amalgam "feel", the particles are ground to a size of less than about 80 microns. At this size, the particles generally retain a fibrous form, that is, a length greater than their diameter.

The polymeric matrix portion of the dental composite is selected from those known in the art of dental materials, including but not being limited to expandable monomers, liquid crystal monomers, ring-opening monomers, polyamides, acrylates, polyesters, polyolefins, polyimides, polyarylates, polyurethanes, vinyl esters or epoxy-based materials. Other polymeric matrices include styrenes, styrene acrylonitriles, ABS polymers, polysulfones, polyacetals, polycarbonates, polyphenylene sulfides, and the like. These polymeric matrices are derived from curing polymeric matrix precursor compositions. Such precursor compositions are well-known in the art, and may be formulated as one-part, two-part, or other compositions, depending on the components.

Preferred materials include those based on acrylic and methacrylic monomers, for example those disclosed in U.S. Pat. Nos. 3,066,112, 3,179,623, and U.S. Pat. No. 3,194,784 to Bowen; U.S. Pat. Nos. 3,751,399 and 3,926,906 to Lee et al.; and commonly assigned U.S. Pat. No. 5,276,068 to Waknine and U.S. Pat. No. 5,969,000 to Yang, all of which are herein incorporated by reference in their entirety. Especially preferred methacrylate monomers include the condensation product of bisphenol A and glycidyl methacrylate, 2,2'-bis [4-(3-methacryloxy-2-hydroxy propoxy)-phenyl] propane (hereinafter abbreviated BIS-GMA), the condensation product of ethoxylated bisphenol A and glycidyl methacrylate, (hereinafter EBPA-DMA), and the condensation product of 2 parts hydroxymethylmethacrylate and 1 part triethylene glycol bis(chloroformate) (hereinafter PCDMA). Polyurethane dimethacrylates (hereinafter abbreviated to PUDMA) are also commonly-used principal polymers suitable for use in the present invention.

The polymeric matrix precursor composition may further comprise a co-polymerizable diluent monomer. Such monomers are generally used to adjust the viscosity of the polymerizable composition, which affects wettability of the composition. Suitable diluent monomers include, without limitation, hydroxyalkyl methacrylates, such as 2-hydroxyethyl methacrylate, 1,6-hexanediol dimethacrylate, and 2-hydroxypropyl methacrtylate; glyceryl dimethacrylate; ethyleneglycol methacrylates, including ethyleneglycol methacrylate, diethyleneglycol dimethacrylate, triethyleneglycol dimethacrylate and tetraethyleneglycol dimethacrylate; or diisocyanates, such as 1,6-hexamethylene diisocyanate. Triethyleneglycol dimethacrylate (TEGDMA) is particularly preferred for use in the present invention.

The polymeric matrix precursor composition typically includes polymerization initiators, polymerization accelerators, ultra-violet light absorbers, anti-oxidants, fluorescent whitening agents, and other additives well known in the art. The polymer matrices may be visible light curing, self-curing, dual curing, and vacuum-, heat-, and pressure-curable compositions as well as any combination thereof. Visible light curable compositions employ light-sensitive compounds such as benzil diketones, and in particular, dl-camphoquinone in amounts ranging from about 0.05 to 0.5 weight percent. UV absorbers are particularly desirable in the visible light curable compositions in order to avoid discoloration of the resin form any incident ultraviolet light. Suitable UV absorbers are the various benzophenones, paticularly UV-9 and UV-5411 available from American Cyanamid company, and benzotriazoles known in the art, particularly 2-(2'-hydroxy-5'-methylphenyl)-benzotriazole, sold under the trademark TINUVIN P by Ciba-Geigy Corporation, Ardsley, N.Y. in amounts ranging from about 0.05 to about 5.0 weight percent.

In the self curing compositions, a polymerization accelerator may be included in the polymerizable monomer composition. The polymerization accelerators suitable for use include the various organic tertiary amines well known in the art, generally aromatic tertiary amines, such as dimethyl-p-toluidine, dihydroxyethyl-p-toluidine and the like, in amounts ranging from about 0.05 to about 4.0 weight percent, and generally acrylate derivatives such as dimethylaminoethyl methacrylate and particularly, diethylaminoethyl methacrylate in amounts ranging from about 0.05 to 0.5 weight percent.

The heat and pressure curable compositions include, in addition to the monomeric components, a heat cure initiator such as benzoyl peroxide, 1,1'-azobis (cyclohexanecarbonitrile), or other suitable free radical initiators. Particularly suitable free radical initiators are lauroyl peroxide, tributyl hydroperoxide, 2,2'-azobisisobutyronitrile ("AIBN") and, more particularly benzoyl peroxide or 1,1'-azobis(cyclohexanecarbonitrile).

The total amount of filler is determined by the specific function of the filled materials, being in the range from about 5 to 95% by weight of the total composite composition. Preferably, the composites of the present invention may also include other inorganic and/or organic fillers or a mixtures thereof currently used in dental restorative materials. When used as a direct filling material, the desired amalgam "feel" is obtained by using about 10 to about 60% by weight of ground, densified, embrittled glass fiber and from about 30 to about 80% by weight of other filler, for example barium borosilicate. A preferred composition comprises about 15% by weight of a resin mixture comprising EBP-DMA and PCDMA in a ratio of 70:30 by weight, about 35% by weight of ground, densified, embrittled glass filler, and about 50% by weight of barium borosilicate filler.

Examples of other suitable filling materials include, but are not limited to, silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide and titania. Suitable fillers for dental filling-type materials prepared in accordance with this invention are those having a particle size ranging from about 0.1–5.0 microns with a silicate colloid of 0.001 to about 0.07 microns and prepared by a series of milling steps comprising wet milling in an aqueous medium, surface etch milling and silanizing milling in a silane solution. Some of the aforementioned inorganic filling materials are disclosed in U.S. Pat. Nos. 4,544,359 and 4,547,531, pertinent portions of which are incorporated herein by reference.

Figure 1:
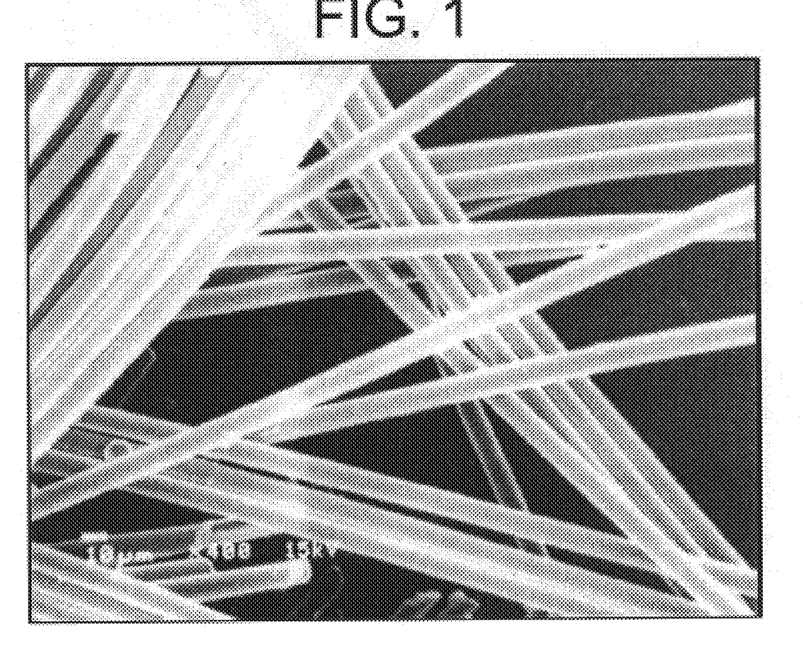
FIG. 1 is a photomicrograph of glass fibers before heating the glass fibers in accordance with the present invention.
Figure 2:
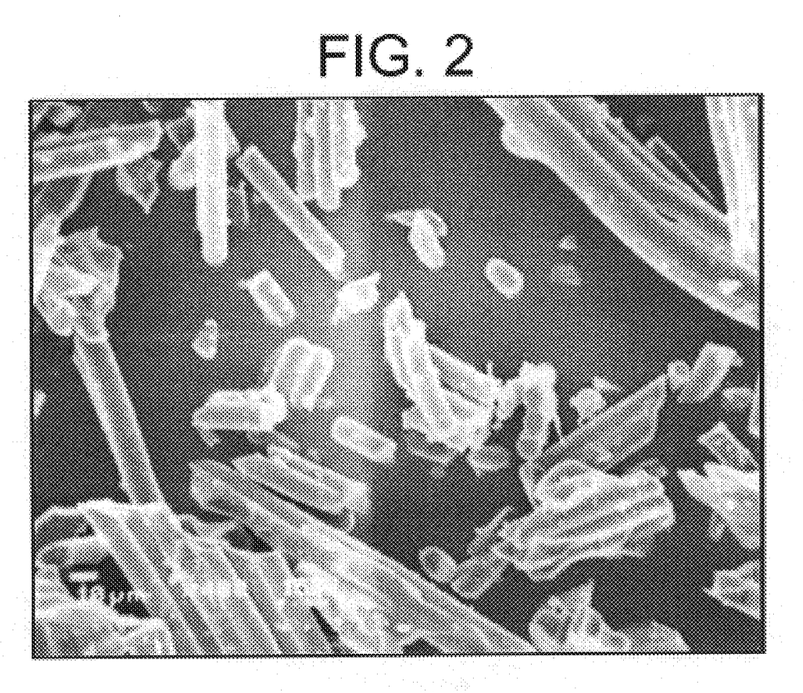
FIG. 2 is a photomicrograph of the densified, embrittled glass fibers after the glass fibers have been heated substantially below the softening point of the glass fibers.
Figure 3A:
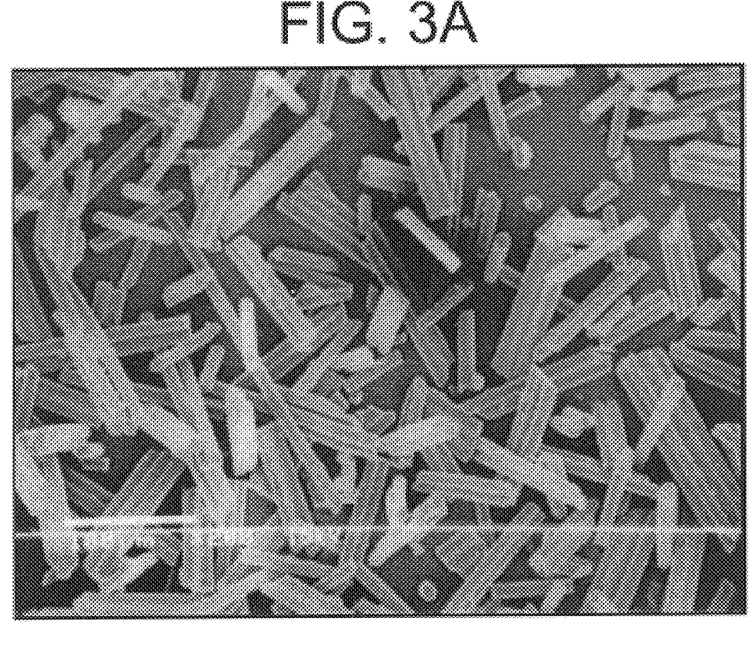
FIGS. 3A and 3B are photomicrographs at an (A) 10 micron and (B) 100 micron scale of the densified, embrittled glass fibers after grinding to a particle size of less than about 80 $\mu$m.
Figure 3B:
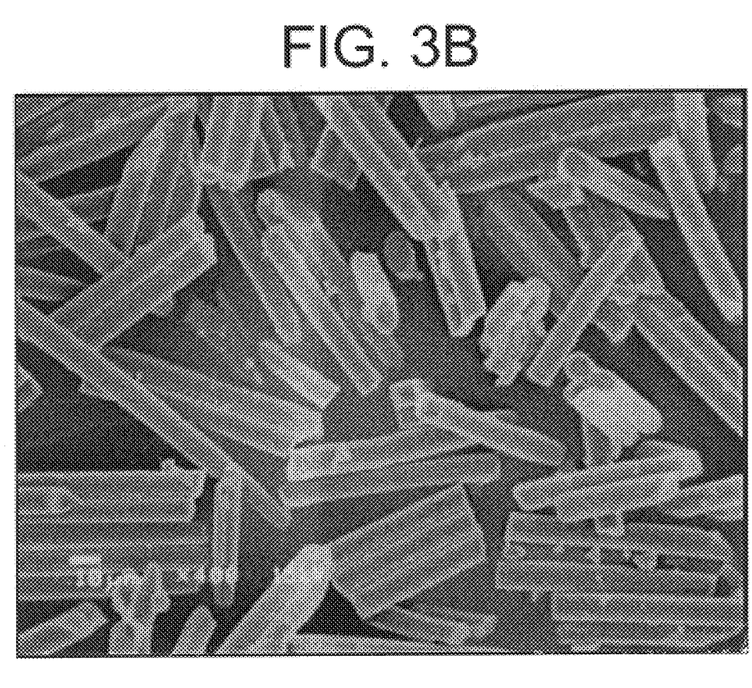

Referring now to the drawings wherein like numerals indicate like elements, FIG. 1 is a photomicrograph of S-2® glass fibers 10 before the fibers have been densified and embrittled. FIG. 2 illustrates S-2® glass fibers 12 which have been densified and embrittled by heating the glass fibers at a temperature substantially below the softening point of the glass fibers in accordance with the present invention. The glass fibers 12 are not fused or melted. FIGS. 3A and 3B are photomicrographs illustrating the densified, embrittled glass fibers 14 of the present invention after grinding.

The dental composites of the present invention provide improved handling characteristics, physical properties, and provide an attractive substitute to dental amalgam alloys as direct filling materials. Elastic modulus, Vicker's hardness, water sorption, polymerization shrinkage and depth of cure were measured for the dental composites of the present invention according to ANSI/ADA Specification No. 27 and Addendum 1 thereof for Resin-Based Filling Materials.

Figure 4:
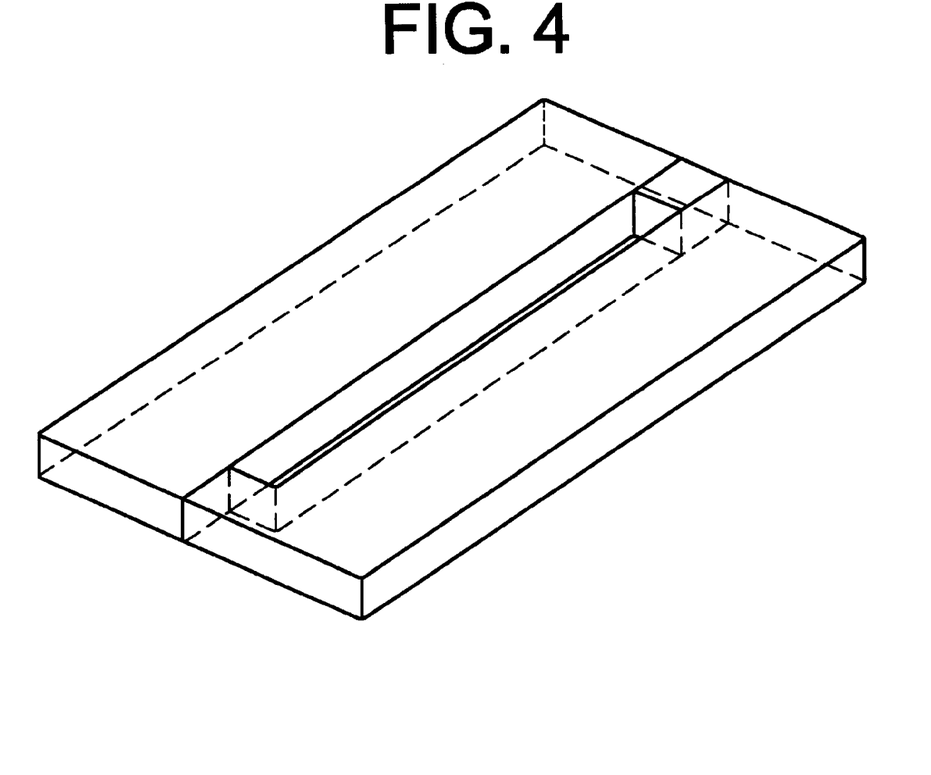
FIG. 4 is a mold for flexural strength testing.

In accordance with the ANSI/ADA Specification No. 27 Section 7.8 Flexural Properties, a test specimen comprising the Type 1 dental composite material was prepared using a mold as shown in FIG. 4. Type 1 materials are chemically cured materials, i.e., those materials where setting is effected by mixing an initiator and activator, but excluding those materials where setting is also effected by the application of energy (dual cure materials). Preparation of the test specimen was carried out in time intervals measured from the start of mixing, i.e., start timing the moment mixing of the dental composite material has begun. The dental composite material, manufactured according to the methods described herein, was placed in the mold on one of two glass slides, each having sufficient surface area to cover the mold. The second glass slide was placed on top of the dental composite material and mold. Pressure was applied to the mold using a clamp until excess dental composite material was exuded. Three minutes after the start of mixing the clamped mold assembly was placed in a water bath, maintained at 37±1° C. Fifteen minutes after the start of mixing the mold assembly was then removed from the bath, the clamp was removed from the mold assembly, and the test specimen was removed from the mold. The test specimen was then stored in distilled water maintained at a temperature of 37±1° C. After 23 hours and 45 minutes passed from the start of mixing, the dental composite test specimen measured 25±2 millimeters (mm) by 2±0.1 mm by 2±0.1 mm at a temperature of 37±1° C.

A second test specimen comprising Type 2 dental composite material was prepared according to the steps for preparing a Type 1 test specimen prior to removing the specimen from the mold. Type 2 materials are external-energy activated materials, i.e., those materials where setting is effected by the application of energy, such as blue light and including those materials which also contain a chemical initiator and activator. An external energy source as known to one of ordinary skill in the art was placed against the glass slide at the center of the test specimen. That section of the test specimen was irradiated for the recommended exposure time as known to one of ordinary skill in the art. The external energy source was then positioned against the glass slide over another section of the test specimen, which slightly overlapped the irradiated center section, and the test specimen was irradiated again for the recommended exposure time. This procedure was repeated until the entire length of the test specimen was irradiated. The procedure was then performed on the other side of the test specimen using the same steps, until the entire length of the other side was irradiated. The assembly was then placed in a water bath maintained at 37±1° C. for 15 minutes. The test specimen was removed from the mold and stored in distilled water at 37±1° C.

To measure the elastic modulus the dental composite test specimens were positioned in a flexural strength testing apparatus. The flexural strength testing apparatus comprised two rods, mounted parallel with 20 mm between their centers, and a third rod centered between, and parallel to, the other two rods, so that the three rods in combination were used to give a three-point loading to the specimen. Twenty-four hours after the start of mixing, a load was applied to the test specimens at a cross-head of 0.75±0.25 millimeters per minute (mm/min) or at a rate of loading of 50±16 Newtons per minute (N/min) until the specimen fractured. The flexural modulus, E, in megapascals, was calculated using the following equation:

$$E = \frac{F_l \beta}{4bh^3 d}$$

where $F_1$ is the load, in newtons; d is the deflection (mm) at load $F_1$; l is the distance (mm) between the supports, accurate to ±0.01 mm, b is the width (nm) of the test specimen measured immediately prior to testing; and, h is the height (mm) of the test specimen measured immediately prior to testing.

The dental composite test specimens exhibited a modulus of elasticity of greater than approximately 15 GPa and modulus range between approximately 15 and approximately 22 GPa. These test results indicate that the dental composite possesses a modulus of elasticity value much higher than conventional dental composites, which possess an elastic modulus of approximately 10 GPa. The elastic modulus of the dental composite of the present invention is comparable to amalgam, which exhibits an elastic modulus of approximately 20 GPa. A relatively low modulus may cause a temporary displacement of the restoration resulting from normal masticatory stresses. Eventually this may cause leakage that may lead to secondary caries. Such movement or displacement is less likely to occur with materials having a high elastic modulus such as the composite of the present invention.

In accordance with the ANSI/ADA Specification No. 27 Section A2.2 Compressive Strength, a Type 1 test specimen was prepared using a split metal mould, coated with an appropriate separating medium (e.g., spectroscopic grease) for the preparation of a cylindrical test specimen. The dental composite material was placed in the mold on one of two glass slides, each having sufficient surface area to cover the mold. The second glass slide was placed on top of the dental composite material and mold. Pressure was applied to the mold using a clamp until excess dental composite material was exuded. Three minutes after the start of mixing the clamped mold assembly was placed in a water bath maintained at 37±1° C. Fifteen minutes after the start of mixing the mold assembly was removed from the bath, and the test specimen removed from the mold. The test specimen was then stored in distilled water maintained at a temperature of 37±1° C. After 23 hours and 45 minutes passed from the start of mixing, the dental composite test specimen measured 4.0±0.1 mm in diameter by 6.0±0.1 mm in height.

A Type 2 dental composite test specimen was prepared according to the steps for preparing a Type 1 test specimen, prior to removing the test specimen from the mold. An external energy source was placed against the glass slide and over the test specimen in the mold. The specimen was irradiated for the recommended exposure time as known to one of ordinary skill in the art. The mold was then inverted to irradiate the other side of the test specimen. After the test specimen was irradiated, the assembly was placed in a water bath maintained at 37° C. for 15 minutes. The specimen was removed from the mold and stored in distilled water at 37° C. If the dental composite material's depth of cure is less than 3.0 mm, or the depth of cure when determined according to ISO 4049 Section 7.7 is less than 3.0 mm, then a quartz glass mold should be used to allow lateral exposure of the test specimen.

To measure the compressive strength the dental composite test specimens were placed in a compression platen testing machine 23 hours and 45 minutes after the start of mixing. The compression platen testing machine comprised an apparatus capable of applying a uniaxial compressive loading at a strain of 1.0±0.25 mm/min. Twenty-four hours after the start of mixing the composite material, a load was applied to the test specimen at a strain rate of 1.0±0.25 mm/min. The compressive strength, i.e., Vicker's hardness, in Newtons per millimeter squared, or megapascals (MPa), was calculated using the following equation:

$$\text{Compressive strength} = \frac{F}{d^2}$$

where F is the maximum force in Newtons exerted on the test specimen; and, d is the diameter of the test specimen in millimeters.

The dental composite exhibited a Vicker's hardness of approximately 1,250 MPa. This Vicker's hardness value indicates that the dental composites are able to withstand stress better than conventional dental composites having a hardness value in the range of 600 to 700 MPa. In addition, the dental composite's wear rate is very low, averaging about 3.5 microns per year, which is comparable to that exhibited by amalgam.

Figure 5:
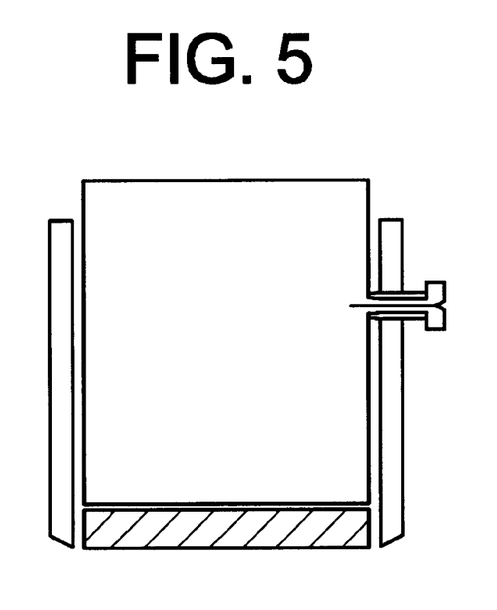
FIG. 5 is a mold for water sorption and solubility test.

In accordance with the ANSI/ADA Specification No. 27 Section 7.9 Water Sorption and Solubility, a Type 1 test specimen was prepared using the mold shown in FIG. 5. The mold was slightly overfilled with the dental composite material. A piece of film 50±30 μm thick, e.g., polyester, was placed over the material. A glass slide was placed on top of the film, and excess dental composite material was exuded from the mold. The slide and mold assembly were then clamped, and pressure was applied to form a test specimen disc.

A Type 2 dental composite test specimen was prepared according to the steps for preparing a Type 1 test specimen, prior to removing the specimen from the mold. An external energy source known to one of ordinary skill in the art was placed against a glass slide and over the test specimen in the mold. That section of the test specimen was irradiated for the recommended exposure time as known to one of ordinary skill in the art. The external energy source was then positioned against the glass slide over another section of the test specimen, which slightly overlapped the irradiated section, and the test specimen was irradiated again for the recommended exposure time. This is procedure was repeated until the entire test specimen was irradiated for the recommended exposure time.

The dental composite test specimen discs were placed in a dessicator maintained at 37±1° C., and containing anhydrous calcium chloride or silica gel freshly dried for 5 hours at 130° C. The test specimens were removed from the dessicator after 24 hours, and then stored in a second desiccator maintained at 23±1° C. for 1 hour. The test specimens were then weighed repeatedly, i.e., reconditioned, until the mass loss of the test specimen was not more than 0.2 milligrams in any 24 hour period. The test specimens were then immersed in water maintained at 37±1° C. for 7 days. The test specimens were removed, washed with water, and blotted until the test specimens were free from visible moisture. Each test specimens was then weighed one minute after being waived in air for 15 seconds. The diameter of each test specimen was measured, and the thickness of each test specimen was measured at its center and at four equally spaced points along their circumferences. The water sorption $w_{sp}$, in micrograms per cubic millimeter, was calculated using the following equation:

$$w_{sp} = \frac{m_2 - m_3}{v}$$

where $m_2$ is the mass of the specimen, in micrograms ($\mu$g), after immersion in water for 7 days; $m_3$ is the reconditioned mass of the specimen, in micrograms ($\mu$g); and, V is the volume of the specimen, in cubic millimeters. The dental composite test specimen exhibited a water sorption value of approximately 8.9 micrograms per cubic millimeter per week ($\mu$g/mm$^3$/wk).

In accordance with the ANSI/ADA Specification No. 27 Section A2.4 Polymerization Shrinkage, a Type 1 test specimen was prepared by first determining the volume of capillary per mm division of a glass dilatometer tube. The tube has a length approximately 250 mm graduated in divisions of 1 mm with a ground glass end containing a capillary of uniform diameter approximately 0.7 mm. The tube was filled to different levels with mercury to determine the volume of the capillary. Once the volume is determined, the tube was fitted into a density bottle. The density bottle and dilatometer tube were immersed in a water bath maintained at 25±0.1 C. for at least two hours prior to testing the specimen. Approximately 10 mm$^3$ of the dental composite material was mixed, and placed in the density bottle in the bath. The dilatometer tube was removed from the water bath, and a stream of air was blown through the capillary to remove any remaining water. The tube was placed into the bottle, sealed, and wiped off to remove excess displaced water. The top of the tube remained just above the water level in the bath. At 90 seconds from the start of mixing, a base reading of the meniscus level in the capillary tube [$H_1$] was recorded. The meniscus level was recorded at 1 hour after the start of mixing [$H_2$]. The volume change of the specimen was calculated using the formula V=[$H_1$-$H_2$]×A. The volume [V] of the specimen at room temperature was determined using a second density bottle as follows: determine the mass of the dry specimen [M1], the mass of the density bottle filled with water [M2], and the mass of the density bottle filled with the test specimen and water [M3]. The mass of water displaced was calculated using the formula [M1+M2−M3]. The volume of the test specimen was calculated using the formula [M1+M2−M3] divided by the density of water at the ambient temperature.

When preparing a Type 2 test specimen, the body of a density bottle having a removable cover was covered with black adhesive tape, leaving an aperture 1.5 square centimeters. The volume of a capillary tube was determined per mm division by weighing the tube filled to different levels with mercury. The density bottle with cover and dilatometer tube was immersed in a water bath maintained at 25±0.1 C. for at least 2 hours prior to testing the test specimen. The tube was removed from the bath, and a stream of air was blown through the capillary tube to remove any remaining water. Approximately 10 mm$^3$ of the test material was placed into the density bottle such that the material lied near the aperture. The tube was placed into the density bottle. The bottle was sealed and wiped to remove any excess displaced water. The top of the tube remained just above the water level in the bath. Meniscus readings were recorded until the meniscus remained stable such that a first reading [$H_1$] was recorded based upon 3 readings at 2 minute intervals which did not differ by more than 0.1 mm each. The aperture cover was then removed and the test specimen irradiated through the density bottle. The test specimen was irradiated with the recommended light known to one of ordinary skill in the art for at least four times for the recommended time period known to one of ordinary skill in the art. The meniscus level was read at 1 hour after irradiation to record a second reading [$H_2$]. The volume of the test specimen was calculated according to the steps for the Type 1 test specimen.

The percent polymerization shrinkage of the test specimen is calculated using the following equation:

$$S = \frac{V}{V + V'} \times 100\%$$

where s is the percent polymerization shrinkage; and, V is the specimen volume. The dental composite test specimen exhibited a polymerization shrinkage by volume of approximately 1.98%.

In accordance with ANSI/ADA Specification No. 27 Section 7.7 Depth of Cure, a Type 2 dental composite test specimen was prepared using a mold. The mold was placed on a strip of film having a thickness of 50±30 $\mu$m, and transparent to the activating radiation, e.g., polyester, that covered a piece of white filter paper. The mold was slightly overfilled with dental composite material such that the material was free of air bubbles. A second strip of transparent film was placed on top of the mold. The assembly was placed between two glass slides, each having a sufficient area to cover one end of the mold, and pressed to exude excess dental composite material. The glass slide covering the strip of transparent film was removed. An external energy source as known to one of ordinary skill in the art was placed against the transparent film, and the dental composite material was irradiated for a time sufficient to achieve a depth of cure of at least 2 mm. The dental composite test specimen was then removed from the mold, and its height was measured with a micrometer to record the depth of cure.

The dental composite exhibited a depth of cure of at least 5 mm due in part to the glass fibers used in the filler component, which allow for bulk-fill application. The glass fibers serve as transparent pipes, which transmit light to the bottom of the restoration. The composites allow use of mechanical packing and condensing with its attendant advantages. The ground, densified, embrittled glass fiber filler of the present invention may further be utilized in numerous other applications in the practice of dentistry, including periodontal splitting, tooth replacement, tooth stabilization, bridge manufacture, and the like. All of these will not be described herein, as such dental operations are well known to those practicing dentistry, i.e. those of ordinary skill in the art.

While preferred embodiments have been shown and described, various modifications and substitutions may be made thereto without departing from the spirit and scope of the invention. Accordingly, it is to be understood that the present invention has been described by way of illustrations and not limitation.

What is claimed is:
1. A dental restoration comprising:
   a polymeric material; and
   a filler material, wherein the filler material comprises ground, densified, embrittled glass particles;
   wherein the restoration has an elastic modulus of greater than approximately 15 GPa.
2. The restoration of claim 1, wherein
   the elastic modulus is between approximately 15 GPa and approximately 22 GPa.
3. The restoration of claim 2, wherein
   the polymeric material is formed from a precursor material that comprises at least one acrylate or methacrylate monomer.

4. The restoration of claim 3, wherein the filler material comprises ground, densified, embrittled glass particles, wherein the particles are derived from glass fibers heated at a temperature substantially below the softening point of the glass fibers for a period of time effective to densify and embrittle the glass fibers, the densified, embrittled glass fibers being subsequently ground.

5. The restoration of claim 4, wherein the glass fibers have a composition comprising about 64–66% $SiO_2$, 24–25% $Al_2O_3$, 0–0.1% CaO, 9.5–10% MgO, 0–0.2% $Na_2O+K_2O$, and 0–0.1% $Fe_2O_3$.

6. The restoration of claim 5, wherein the ground, densified, embrittled glass particles have an average particle size of less than about 80 microns.

7. The restoration of claim 6, wherein the ground, densified, embrittled glass particles comprise from about 5% to about 95% by weight of the total composite composition.

8. The restoration of claim 7, wherein the ground, densified, embrittled glass particles comprise about 35% by weight of the total composite composition.

9. The restoration of claim 8, wherein the dental composite comprises at least one additional filler material.

10. The restoration of claim 9, wherein the at least one additional filler material is at least one of silica, silicate glass, quartz, barium silicate, strontium silicate, barium borosilicate, borosilicate, lithium silicate, amorphous silica, ammoniated or deammoniated calcium phosphate, alumina, zirconia, tin oxide or titania.

11. The restoration of claim 10, wherein the at least one additional filler material is barium borosilicate, comprising between about 5% to about 95% by weight of the total composite composition.

12. A dental composite comprising:

a polymeric material; and a filler material, wherein the filler material comprises ground, densified, embrittled glass particles;

wherein the composite has a Vicker's hardness of at least 1000 MPa.

13. A dental composite comprising:

a polymeric material; and a filler material, wherein the filler material comprises ground, densified, embrittled glass particles;

wherein the composite has a Vicker's hardness of at least 1000 MPa.

14. A dental composite comprising:

a polymeric material; and a filler material, wherein the filler material comprises ground, densified, embrittled glass particles;

wherein the composite has a depth of cure of at least 5 mm.

15. A dental composite comprising:

a polymeric material; and a filler material, wherein the filler material comprises ground, densified, embrittled glass particles;

wherein the composite has a water sorption less than approximately 10 $\mu g/mm^3$/wk.

* * * * *

UNITED STATES PATENT AND TRADEMARK OFFICE
CERTIFICATE OF CORRECTION

PATENT NO.   : 6,403,676 B1
DATED        : June 11, 2002
INVENTOR(S)  : Jia et al.

It is certified that error appears in the above-identified patent and that said Letters Patent is hereby corrected as shown below:

Column 1,
Line 42, delete "on" and insert -- of --.
Line 49, delete "polyarylates" and insert -- polyacrylates --.

Column 2,
Line 18, delete "filing" and insert -- filling --.
Line 39, delete "is".
Line 52, delete "fillers" and insert -- filler --.
Line 66, delete "to" and insert -- that of --.

Column 4,
Line 9, delete "drawing" and insert -- drawings --.
Line 53, between "but" and "being" insert -- not --.

Column 5,
Line 56, delete "polyarylates" and insert -- polyacrylates --.

Column 6,
Line 40, delete "methacrtylate" and insert -- methacrylate --.
Line 60, delete "form" and insert -- from --.
Line 63, delete "company" and insert -- Company --.

Column 7,
Line 24, delete "mixtures" and insert -- mixture --.

Column 9,
Line 29, delete "mould" and insert -- mold --.

Column 10,
Line 45, delete "is".
Line 61, delete "specimens" and insert -- specimen --.

UNITED STATES PATENT AND TRADEMARK OFFICE
CERTIFICATE OF CORRECTION

PATENT NO. : 6,403,676 B1
DATED : June 11, 2002
INVENTOR(S) : Jia et al.

It is certified that error appears in the above-identified patent and that said Letters Patent is hereby corrected as shown below:

Column 14,
Lines 12-19, delete claim 13.

Signed and Sealed this

Seventeenth Day of January, 2006

JON W. DUDAS
*Director of the United States Patent and Trademark Office*